United States Patent [19]

Walbeoffe-Wilson et al.

[11] 4,406,290

[45] Sep. 27, 1983

[54] WRIST-TYPE PULSE MONITOR

[76] Inventors: John H. Walbeoffe-Wilson, Colston House, Buckfastleigh, South Devon County; Julian D. Lynn-Evans, 5 St. John's St., Chichester, West Sussex; Patrick D. Wright, 7 Priors Ct. St. John's Rd., Woking, Surrey, all of England

[21] Appl. No.: 234,740

[22] Filed: Feb. 17, 1981

Related U.S. Application Data

[63] Continuation of Ser. No. 42,046, May 24, 1979.

[51] Int. Cl.³ ............................................. A61B 5/02
[52] U.S. Cl. .................................. 128/689; 128/690
[58] Field of Search ....................................... 128/690

[56] References Cited

U.S. PATENT DOCUMENTS

| 4,096,854 | 6/1978 | Perica et al. | 128/690 |
| 4,210,294 | 10/1978 | Wolfe | 128/690 X |
| 4,239,048 | 12/1980 | Steuer | 128/690 X |

FOREIGN PATENT DOCUMENTS 2736541  2/1979  Fed. Rep. of Germany ...... 128/706

OTHER PUBLICATIONS

Atherton, J., "An Instantaneous Ratemeter With Digital Display", MBE, vol. 13, No. 5, pp. 669-673, Sep. 1975.

Timmerman, G., "HR Monitor Captures VLF Signals".
Stotts, L. J. et al., "Digital Beat-To-Beat Cardiotachometer", Amer. Jrnl. Phys. Med. ©1979, Williams & Wilkins (Apr. 1979, vol. 58, #2, pp. 86-90).
Reddy, P. et al., "All-Digital Instantaneous HR Meter", MBE & Computing, Jul. 1977, pp. 472-473.
Taylor, K. D. et al., "Precision Digital Instantaneous Cardiotach Using C.M.O.S. IC's, MBEC 1979, vol. 17, pp. 786-788.
Hartley, R. W. et al., "Analog Display Rate Meter Built Around Digital Switching Elements", MBE Jan. 1976, pp. 107-108.

*Primary Examiner*—Kyle L. Howell
*Assistant Examiner*—Francis J. Jaworski
*Attorney, Agent, or Firm*—Sigalos & Levine

[57] ABSTRACT

A wrist-type pulse monitor for providing a digital readout of the rate of a heartbeat comprising a sensor adapted to detect a heartbeat in a body region where a heartbeat pulse normally occurs, a transducer coupled to the sensor for transforming each detected pulse into an electrical signal, an oscillator for producing electrical pulses at a predetermined frequency, means coupled to the transducer and the oscillator for counting the number of oscillator pulses occurring between detected heartbeats, arithmetic means coupled to the counting means for converting the heartbeat counted oscillator pulses to a heartbeat rate and means for visually displaying the heartbeat rate in digital form.

14 Claims, 5 Drawing Figures

WRIST-TYPE PULSE MONITOR

This is a continuation, of application Ser. No. 042,046, filed May 24, 1979.

BACKGROUND OF THE INVENTION

This invention relates to a portable, preferably wrist-mounted, device for monitoring heartbeat or pulse rate. Various physical exercises, and in particular those such as jogging which are practiced by individuals having widely varying ages and fitness factors, are beneficial only if performed within the range of levels which are reflected by the desired pulse rate of a given individual. If the individual's pulse rate does not rise to a particular lower level, the exercise may be of little effect whereas the effects can be decidedly harmful if an upper level is exceeded.

Prior art devices exist which monitor the beat of the human heart such as the monitor disclosed in U.S. Pat. No. 3,742,937. However, in that particular case, a visible light pulse is produced for each heartbeat measured during a fifteen second interval. Thus, once the light begins flashing, the flashing will continue for fifteen seconds and the user of the monitor must count the flashes from the light and multiply by four to obtain his present heart rate in beats per minute. A readout is, of course, extremely inconvenient to obtain and is subject to error in that the user may either miscount the flashes of light or make a mistake in multiplying the number of flashes times four and, thus, may obtain the incorrect or inproper heart rate.

SUMMARY OF THE INVENTION

It is an object of the present invention to provide a simple device which gives a convenient and direct readout of the effects of physical exercises such as jogging on the heartbeat or pulse rate. According to the present invention, there is provided a portable device for monitoring pulse rate comprising a sensor to be applied to the user's body at a point where the heartbeat pulse can be detected, a display unit to be mounted for convenient inspection by the user and electronic means to receive pulses from said sensor, relate said signals to a time base to produce rate signals, and transmit said rate signals to the display unit to be displayed as a pulse-rate readout.

Thus, the invention envisions a wrist-type pulse monitor for providing a digital readout of the rate of a heartbeat comprising a sensor on said monitor adapted to detect a heartbeat in a region where a pulse normally occurs, a transducer coupled to said sensor for transforming each said detected heartbeat into an electrical signal, an oscillator for producing electrical pulses at a predetermined frequency, means coupled to said transducer and said oscillator for counting the number of said oscillator pulses occurring between detected heartbeats, arithmetic means coupled to said counting means for converting said counted oscillator pulses to a heartbeat rate and means for visually displaying said rate in digital form.

BRIEF DESCRIPTION OF THE DRAWINGS

Numerous other aspects of this invention along with additional objectives, features, and advantages of the invention should now become apparent upon a reading of the following exposition in conjunction with the accompanying drawings in which.

DETAILED DESCRIPTION OF THE DRAWINGS

Figure 1:
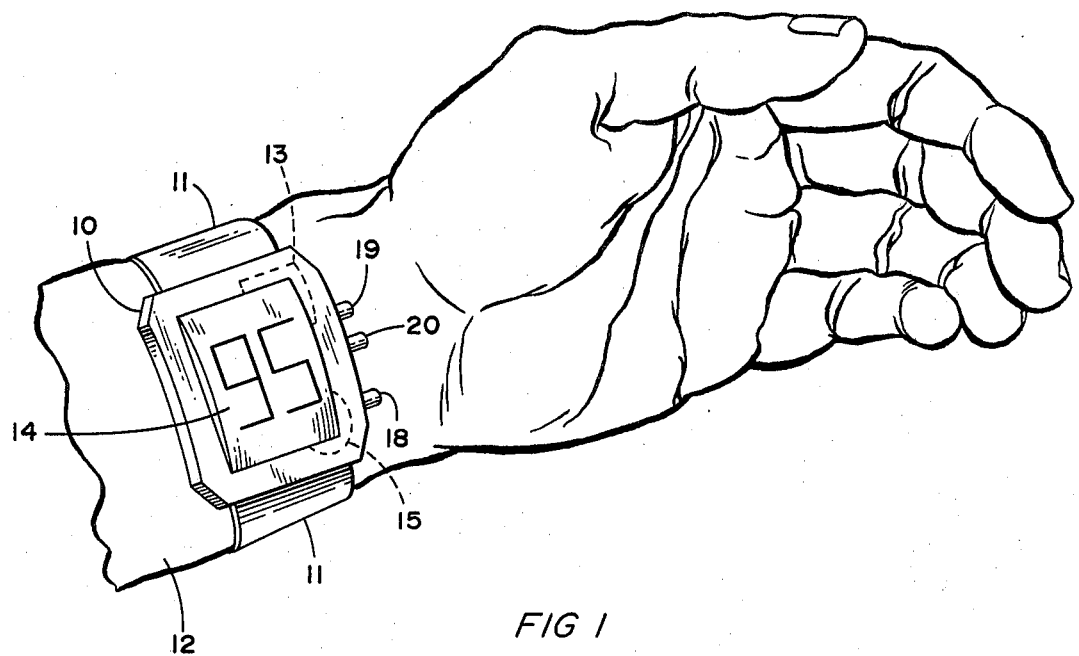
FIG. 1 illustrates a front view of the novel wrist-mounted device for monitoring heartbeat rate.
Figure 2:
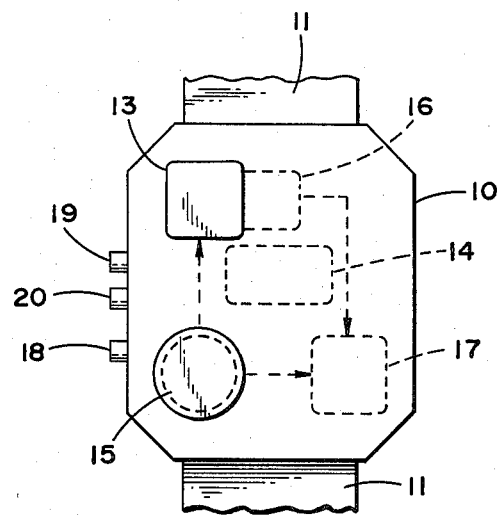
FIG. 2 is a schematic representation of the reverse side of said wrist-mounted pulse or heartbeat monitor.

Preferably, the rate monitor includes a casing having the general form of a wrist watch which carries a sensor at its rear face in a position to contact a pulse point on the user's wrist and presents the heartbeat rate in digital form on the display unit on its front face and has a suitable strap provided to hold the casing to the wrist of the user with the sensor in its correct position. FIG. 1 illustrates the pulse rate monitor attached to the wrist of a user. As can be seen, the monitor comprises a casing 10 which is of substantially the same shape and size as the casing of a wrist watch and to which a wrist strap 11 is secured. Strap 11 is preferably formed of rubber or similar material to provide an effective grip on wrist 12 of the user and thus maintain the casing 10 in the desired position. A pressure sensor 13 of any well known type is mounted in the rear face of the casing 10 in such a position as to lie against the principal pulse point when casing 10 is strapped to wrist 12. The front of casing 10 carries a transparent screen 14 of a display unit which includes a numerical or digital readout. The readout can be a light emitting diode (LED) or a liquid crystal display (LCD) depending upon the type of power supply utilized and the amount of power that must be consumed by the display. The readout should present relatively large and easily read numerals. Casing 10 is also provided with a battery compartment 15 and contains electronic circuitry utilizing generally conventional components. As shown in FIG. 2, the circuitry comprises essentially a transducer 16 which receives pulse movements (caused by the heartbeat) from pressure sensor 13 and transmits corresponding electrical signals to a time base circuit 17 which produces a digital readout.

In actual operation, the user will attach the casing 10 securely to his wrist as shown in FIG. 1 with the sensor 13 directly positioned at the proper pulse point and will then either have a direct readout or press an actuating button 18 to illuminate the display which presents a digital readout of his pulse rate. If the display is of the LCD type, it may have continuous operation because of the low power requirement. Normal pulse rate is about 72 pulses per minute, and, depending upon the individual, exercise should be controlled to raise the rate to a higher value but not to exceed probably 120 pulses per minute. If the pulse rate is not raised enough, the exercise may be of little beneficial effect whereas it may be dangerous to exceed a particular rate, for example, 120 pulses per minute, depending upon the individual. Also, the user can monitor his progress by observing successive pulse rates over a period of time and by noting the time taken for his pulse to return to normal after completion of a particular exercise.

Figure 3:
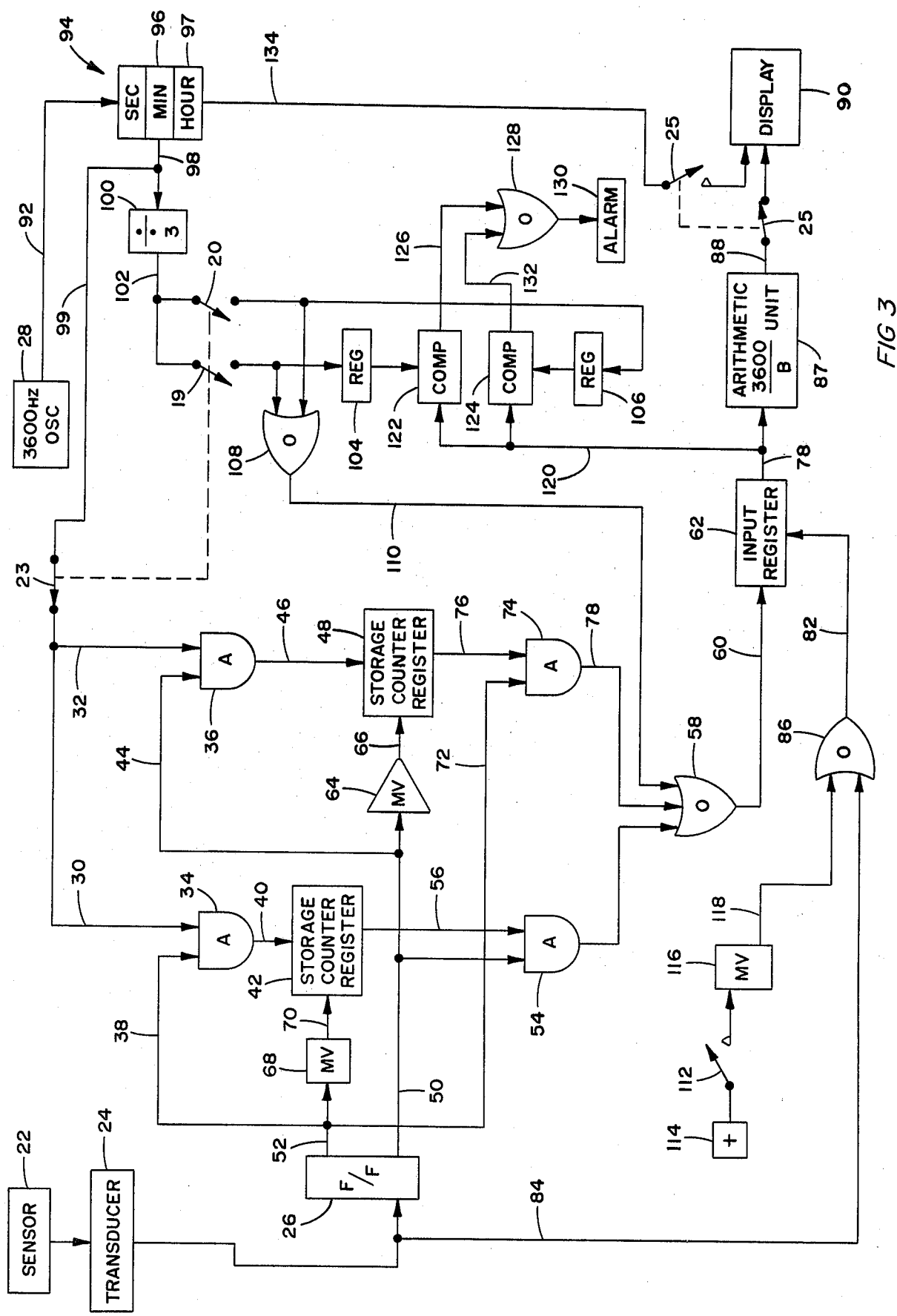
FIG. 3 is a schematic circuit representing the electrical circuit utilized in said wrist-mounted pulse monitor.
Figures 4, 5:
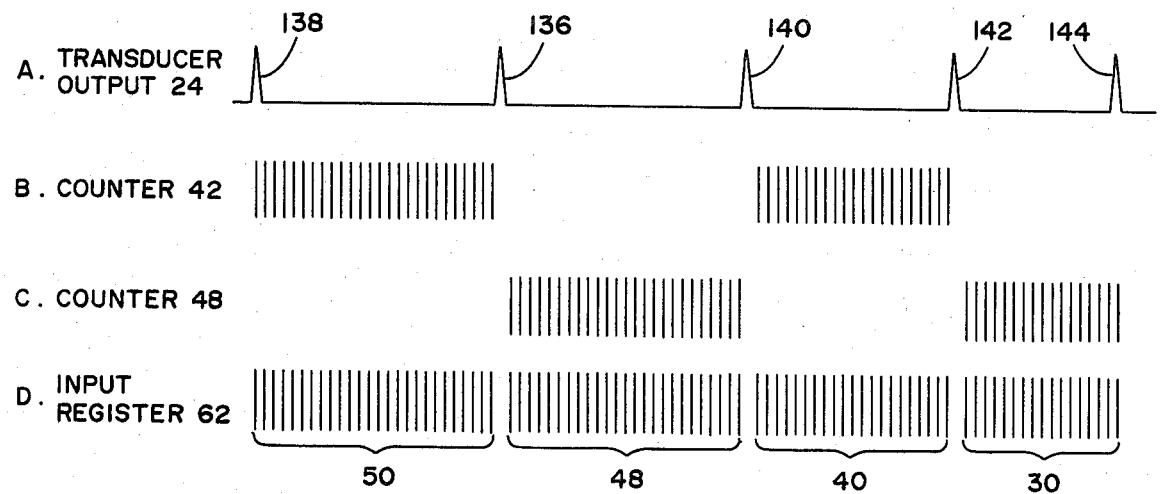
FIG. 4 illustrates various waveforms that appear in the circuit of FIG. 3.
FIG. 5 is a table illustrating the heartbeat rate, H, represented by the number of oscillator pulses, B, stored between heartbeats.

A novel circuit for producing a digital readout of the heartbeat rate is disclosed in FIG. 3. Sensor 22 may be of any of the well-known types of pressure sensors which sense the pulse wave transmitted from the heart. Such a sensor is disclosed in U.S. Pat. No. 3,838,684. The pressure pulse detected by sensor 22 is converted to an electrical signal in a well-known manner by transducer 24. Thus, for each heartbeat pulse detected by sensor 22, the transducer produces an electrical output pulse. This pulse is coupled to a circuit which produces the digital readout representing heartbeat rate. The basic timing unit of the circuit is a 3600 Hz oscillator 28 as shown in FIG. 3. The heartbeat rate per minute is determined by the formula $$H = \frac{3600}{B}$$

where 3600 is simply a unit number, H=heartbeat rate per minute; and B=the number of 60 Hz pulses stored between heartbeats. A comparison of the heartbeat rate, H, and the number of pulses, B, which are stored between heartbeats based upon the above formula is shown in FIG. 5. Thus, if 60 pulses are stored between heartbeats, a heartbeat rate, H, of 60 beats per minute is represented. In like manner, if 120 pulses are stored between heartbeats, a heartbeat rate, H, of 30 beats per minute is represented. Thus, for a range of heartbeat rate from 30 to 180 heartbeats per minute, the pulses that need to be stored between heartbeats ranges from 120 pulses to 20 pulses respectively. Therefore, with an average heartbeat of 72 beats per minute, each heartbeat occurs approximately every 0.83 seconds or, put another way, 1.2 heartbeats occur every second. This being the case, it is convenient to use a 60 Hz signal to represent the pulses, B, being stored between heartbeats. Thus, if 60 pulses were stored between heartbeats, the arithmetic unit 80, in solving the equation set forth above would divide 3600 by the 60 stored pulses to give a heartbeat rate of 60 beats per minute which, of course, is correct.

Oscillator 28 produces its 3600 Hz signal on line 92 which is coupled to a clock circuit 94. Clock circuit 94 is a conventional clock circuit with registers which store signals representing seconds, minutes, and hours. The "seconds", of course, are stored in a well known manner by dividing the input pulses to obtain 3600 seconds representing an hour. The "minute" register 96, however divides those 3600 pulses by 60 to obtain 60 pulses representing minutes and, of course, the "hour" register 97 divides the 60 pulses per minute by 60 to obtain hours. Thus, the output of clock circuit 94 on line 98 represents an output from a divider circuit producing 60 pulses per second. These pulses are coupled via conductor 99 through switch 23 and conductors 30 and 32 to AND gates 34 and 36. AND gates 34 and 36 are enabled by a signal from flip-flop 26 on either line 52 or line 50, respectively. Flip-flop 26 is a bistable multivibrator which changes states each time a pulse is received from transducer 24. Since transducer 24 produces a pulse each time a heartbeat is detected, flip-flop 26 is changing states each time the heart beats. Assume for purposes of example only that flip-flop 26 is set in such an initial state that an output is produced on line 50. This output is coupled through one-shot multivibrator 64 which produces a spike on its output line 66 which is coupled to storage counter register 48 as a clearing signal to clear the register 48. The output signal on line 50 from flip-flop 26 is also coupled via line 44 as an enabling signal to AND gate 36. AND gate 36 now couples the 60 Hz signal on line 99 as an input to storage counter register 48 which begins to store the pulses therein. When the next heartbeat occurs, transducer 24 produces an output signal which changes the state of flip-flop 26. The output on line 50 is removed thus removing the enabling signal to AND gate 36 on line 44 and producing an enabling signal on line 72 to AND gate 74 which also has as the other input thereto the output on line 76 of storage counter register 48. Thus, the input to storage counter register 48 is removed and the output, the contents thereof, is coupled on line 76 through AND gate 74 on line 78 through OR gate 58 on line 60 to input register 62. Thus the pulses that were stored in storage counter register 48 between heartbeats is now stored in input register 62.

Simultaneously, the output of flip-flop 26 on line 52 is coupled as an enabling signal to AND gate 34 which, of course, has as its other input on line 30, the 60 Hz signal. Also, the output of flip-flop 26 on line 52 is coupled to one-shot multivibrator 68 which produces a spike on its output line 70 that clears storage counter register 42. AND gate 34 therefore begins to pass the 60 Hz pulses on line 40 to storage counter register 42 for storage therein. At the same time, since the signal on line 50 from flip-flop 26 has been removed when the flip-flop changed states, the enabling signal has been removed from AND gate 54 and the contents of storage counter register 42 cannot be removed or gated therefrom.

Also, the output of transducer 24 produced by the last heartbeat is coupled via conductor 84 through OR gate 86 on line 82 as an enabling signal to input register 62. Thus, the pulses stored in input register 62 from storage counter register 48 are gated on line 78 into the arithmetic unit 80. Since the arithmetic unit divides 3600 by the number of pulses stored between heartbeats, it produces a signal on line 88 which is coupled to display 90 representing the actual heartbeat rate.

When the next heartbeat occurs, flip-flop 26 is reset and the enabling signal to AND gate 34 on line 38 is removed thus prohibiting further storage of any of the 60 Hz pulses on line 30 into storage counter register 42. At the same time, however, an enabling signal on line 50 from flip-flop 26 enables AND gate 54 thus allowing the contents of storage register 42 to be gated out on line 56 through AND gate 54, OR gate 58 and line 60 to input register 62. As described previously, however, storage counter register 48 is now enabled and begins storing the 60 Hz pulses.

Thus, it can be seen that with the appearance of a heartbeat, one of the counters 42 and 48 begins to store pulses from oscillator 28 until the next heartbeat is produced. At that time, the 60 Hz input pulses from clock circuit 94 are transferred from the first counter to the second counter while the output of the first counter is coupled to an input register 62 for storage purposes. Thus, the number of pulses occurring between heartbeats is stored alternately in counters 42 and 48 and transferred alternately to input register 62.

As stated earlier, in order to properly gate the data stored in input register 62 on line 78 to arithmetic unit 80, a gating signal is required on line 82. This signal can be produced in any well known means but is produced in the preferred manner by coupling the output pulse from transducer 24 on line 84 to OR gate 86, line 82 and input register 62. Thus, each time a heartbeat is detected and transducer 24 produces an electrical pulse on line 84, that pulse is used as a gating signal to gate the information stored in input register 62 to arithmetic unit 80 via line 78.

The arithmetic unit 80 is programmed, as indicated earlier, to divide 3600 by whatever count or number of pulses is stored in input register 62. Thus, as shown in the table in FIG. 5, if input register 62 is storing a count of 20, the arithmetic unit 80 will produce an output on line 88 which represents 180 heartbeats per minute and this output is coupled to display 90 where it is displayed in numerical form. In like manner, if 50 pulses are stored in input register 62, the arithmetic unit 80 will produce an output line 88 representing 72 heartbeats per minute which will be displayed by display 90 in numerical form.

Thus, there has been described and illustrated a novel circuit which will not only monitor the heartbeat of the user but which will produce a digital display of the heartbeat rate at any instant.

It may be important to establish a warning signal if a predetermined upper limit of heartbeat rate is exceeded or a predetermined lower limit of heartbeat rate is not reached. This may be accomplished by storing in a first register a predetermined number of oscillator pulses representing a desired upper limit, for instance 30 pulses which would represent 120 heartbeats per minute and a predetermined number of pulses in a second register representing a lower limit which may be, for example, 60 pulses which would represent 60 heartbeats per minute. By then comparing the contents of each register with the number of pulses stored in input register 62 representing the current heartbeat rate, warning signals may be generated when the upper limit is exceeded or the heartbeat rate does not reach the lower limit. It is desirable to simply have physical contacts on the monitor casing such as a button which can be depressed to establish both the upper and lower limits. Such a circuit is shown in FIG. 3. Thus, the output of oscillator 28 on line 92 is coupled to a clock circuit 94. Clock circuit 94, as stated earlier, has registers for developing signals representing seconds, minutes and hours. Inasmuch as the oscillator 28 is operating at a frequency of 3600 hertz, a "heartbeat" register in clock 94 could divide the input signal and store 60 pulses per second. However, if 60 pulses per second were to be stored in a register representing upper or lower limits, the user would not be able to accurately determine when the desired number of pulses has been stored because 60 pulses would occur in just one second. For that reason, the output of the "heartbeat" register on line 98 is coupled to a divider circuit 100 which divides the number of pulses being received by any convenient number but, in the preferred example, by three which would enable the output of divider circuit 100 to be twenty pulses per second on line 102. Thus, the output of divider circuit 100 on line 102 may be coupled either to switch 19 or to switch 20. If switch 19 is actuated, it couples the 20 pulses per second on line 102 to storage register 104 which stores pulses representing the predetermined upper limit heartbeat rate desired. If switch 20 is actuated, the pulses from divider circuit 100 on line 102 are coupled to register 106 which stores pulses representing the predetermined lower limit heartbeat rate desired. Switches 19 and 20 are so arranged with switch 23 coupled to the input of counters 42 and 48 that whenever either switch 19 or 20 is actuated, switch 23 is opened to remove the output of oscillator 28 to the counter circuits. Separate switches could, of course, be used. The reason that this is necessary is to be able to utilize the slower occurring pulses (i.e., 20 pulses per second) from divider circuit 100 as the reference source in order to be able to visually observe the display while physically depressing switch 19 or switch 20 until the proper heartbeat rate is reached. Thus, if switch 19 is actuated, thereby coupling the output of divider circuit 100 to register 104, it also opens switch 23 to prevent the output from the "heartbeat" register from going to the counter circuits 42 or 48 and also couples the pulses from divider circuit 100 through OR gate 108 on line 110 to OR gate 58 which produces an output on line 60 to input register 62. Thus, the same pulses that are being stored in register 104, the register storing pulses representing the predetermined upper limit of heartbeat rate, are being coupled to the arithmetic unit 80 for processing so that the display 90 will read directly the heartbeat rate represented by the pulses being stored in register 104. With 20 pulses per second appearing from divider network 100 on line 102, when either switch 19 or switch 20 is depressed, 20 pulses per second are being stored in the corresponding register 104 or 106. This obviously causes a rapid change at display 90. It would require three seconds to store 60 pulses representing 60 heartbeats per minute. If it is desired to have a slower rate of storage of the pulses from the divider network 100 into registers 104 or 106, of course divider network 100 may divide by four, six, or any other desired number instead of three.

To set the lower predetermined limit of heartbeat rate, switch 20 is depressed thus coupling the output from divider circuit 100 on line 102 to register 106. Again, that same output is coupled through OR gate 108, line 110, OR gate 58, line 60 and input register 62 to arithmetic unit 80. In like manner, as long as switch 20 is held depressed, the user may view the display until it reads the appropriate heartbeat rate and then release switch 20.

As stated earlier, when switch 19 or switch 20 is depressed to set the predetermined upper or lower limits of heartbeat rate, it is desirable that no pulses be present from counters 42 and 48. Thus, switch 23 is opened each time either switch 19 or switch 20 is closed, thus preventing any storage through the counting circuit. However, it is necessary that input register 62 be gated at some interval so that the pulses being stored therein may be coupled in a group or unit to the arithmetic unit 80. For this purpose, switch 112 may couple power soource 114 to a multivibrator 116 that produces an ouput on line 118 at predetermined intervals which is coupled by OR gate 86 on line 82 as a gating signal to input register 62. However, multivibrator 116 could be adjusted to any desired frequency to provide a gating signal on line 82 for input register 62.

Once the upper and lower heartbeat rate limits have been established by storing pulses in registers 104 and 106, and the monitor is in operation, the output from input register 62 on line 78 is not only coupled to the arithmetic unit 80 but is also coupled through conductor 120 to comparators 122 and 124. If the number of pulses stored in input register 62 representing the actual heartbeat is greater than the number of pulses stored in register 104, comparator 122 produces an output signal on line 126 which passes through OR gate 128 to alarm 130 which may be an audible alarm to warn the user. In like manner, if the number of pulses stored in input register 62 is less than the number of pulses stored in register 106, then comparator 124 produces an output signal on line 132 which also passes through OR gate 128 to activate alarm 130. Thus, the user may set a predetermined high heartbeat rate and a low heartbeat rate which, if the actual heartbeat rate exceeds the upper limit or does not reach the lower limit, will cause an alarm to be activated and the user alerted.

Inasmuch as clock unit 94 already provides seconds, minutes and hour signals based upon a division of the pulses that it receives from oscillator 28, it is a simple matter to couple those signals on conductor 134 to switch 25 which may selectively couple either the output of the clock circuit 94 which continuously maintains time or the output of arithmetic unit 80 to display 90. Thus, while the pulse monitor is not being used as a pulse monitor it may be utilized as a clock or watch simply by placing switch 25 in the appropriate position.

FIG. 4 illustrates the various waveforms that appear at particular points in the circuit shown in FIG. 3. Graph A illustrates the electrical pulses produced by transducer 24 as each heartbeat is detected by sensor 22. Graph A shows, as an example only, the electrical pulses getting closer together with time indicating that the heartbeat rate is increasing. Graph B illustrates the 60 Hz pulses from clock circuit 94 which are being stored in one of the storage counter registers 42 or 48. Assume, for purposes of example only, that they represent the pulses being stored in counter 42. When electrical pulse 136 is generated by the next heartbeat, flip-flop 26 changes states and graph C shows that the pulses from oscillator 28 are now being stored in storage counter register 48. While those pulses are being stored in register 48, the pulses in storage counter register 42 are gated out and coupled to input register 62 as shown in graph D. Assume that 50 pulses were stored in storage counter register 42 during the interval between pulses 136 and 138 representing an interval between the heartbeats of the user. Fifty pulses, as shown in FIG. 5, represents 72 heartbeats per minute, the average heartbeat of an individual. When electrical pulse 140 occurs, flip-flop 26 again changes state thus causing the 60 Hz pulses from clock circuit 94 to again be stored in counter register 42 while those pulses previously stored in counter 48 as shown in graph C are gated out again to the input register 52 as shown in graph D. This time, however, there are only 48 pulses stored in input register 62. Although not shown in the table in FIG. 5, the heartbeat rate can be calculated from the formula previously given and shown to be 75 beats per minute. Thus, the heartbeat rate is increasing. When electrical pulse 142 occurs, again flip-flop 26 changes states thus causing the 60 Hz pulses from clock circuit 94 to be stored in counter 48 and those pulses stored previously in counter 42 are gated out to input storage register 62. As can be seen in graph D of FIG. 4, 40 pulses were stored in counter 42 during the previous interval. Again, from the table shown in FIG. 5, it can be seen that 40 pulses represent a heartbeat rate of 90 beats per minute. When the next electrical pulse 144 occurs, again, flip-flop 26 changes states thus causing the 60 Hz pulses from clock circuit 94 to be stored in counter 42 and the output of counter 48 transferred or gated to input register 62. From graph D of FIG. 4 it will be seen that 30 pulses were stored during the last cycle in counter 48. Again, from the table shown in FIG. 5 it can be seen that thirty pulses represent a heartbeat rate of 120 beats per minute. Thus, display 90 is continuous and, shows, in the example given, the increase in heartbeat rate as determined by the number of pulses being stored in counter registers 42 and 48 and mathematically determined by arithmetic unit 80.

Thus, the present invention has several advantages over the prior art devices. First, it gives a direct digital read out of the heartbeat rate of the user at any instant. Secondly, predetermined high and low heartbeat rate limits may be set which, if the actual heartbeat rate exceeds or does not reach, activates an alarm to warn the user. Thirdly, these upper and lower predetermined limits are easily set by the user simply depressing an upper limit key or a lower limit key and then reading the display output until the proper predetermined limit is reached and then releasing the button or key. Fourth, the unit can be economically used as a wrist watch inasmuch as a clock circuit already exists within the unit.

While the invention has been described in connection with a preferred embodiment, it is not intended to limit the scope of the invention to the particular form set forth, but, on the contrary it is intended to cover such alternatives, modifications, and equivalents as may be included within the spirit and scope of the invention as defined by the appended claims.

What is claimed is:

1. A wrist-type pulse monitor for providing a digital read out of the rate of a heartbeat comprising:
   a. a sensor adapted to detect a heartbeat, in a region where a heartbeat pulse normally occurs,
   b. a transducer coupled to said sensor for transforming each said detected heartbeat into an electrical signal,
   c. means for producing electrical pulses at a predetermined frequency,
   d. means coupled to said transducer and said pulse producing means for counting the number of said produced pulses occurring between two consecutively detected heartbeats, said pulse counting means comprising:
      i. first and second counters coupled to said pulse producing means and said transducer for alternately counting said pulses between heartbeats,
   e. arithmetic means for converting said counted pulses to a heartbeat rate,
   f. means for alternately coupling the outputs of said counters to said arithmetic means whereby the contents of one counter is converted to heartbeat rate while the other is storing said pulses between detected heartbeats, and
   g. means coupled to said arithmetic means for visually displaying said rate in digital form whereby a continuous heartbeat rate is displayed.

2. A pulse monitor as in claim 1 wherein said pulse producing means includes:
   a. an oscillator having a frequency of 3600 Hz, and
   b. clock circuit means for reducing said oscillator frequency to 60 Hz for maintaining time-of-day in hours, minutes and seconds.

3. A pulse monitor as in claim 2 wherein said arithmetic means comprises:
   a. means for converting said counted 60 Hz pulses to heartbeat rate in accordance with the formula $$H = \frac{3600}{B}$$

where H=heartbeat rate and B=number of 60 hertz pulses counted between heartbeats.

4. A pulse monitor as in claim 3 further including:

a. means for establishing an upper and lower predetermined heartbeat rate limit, b. means coupled to said limit establishing means for providing a warning signal when said actual heartbeat rate is below said lower predetermined rate limit and higher than said upper predetermined rate limit, and c. alarm means coupled to said signal producing means for generating an alarm indication when said warning signal is produced.

5. A pulse monitor as in claim 4 wherein said means for establishing upper and lower predetermined heartbeat rate limits comprises:

a. first and second pulse storage registers respectively, b. pulse divider means for further reducing the frequency of said 60 Hz pulses to a lower predetermined frequency, and c. means coupled to said pulse divider means, said first and second pulse storage registers and said arithmetic means for simultaneously storing a predetermined number of said reduced frequency pulses in a selected one of said registers representing said upper and lower heartbeat rate limits and calculating and displaying the instantaneous heartbeat rate represented by said stored pulses.

6. A pulse monitor as in claim 5 wherein said warning signal producing means comprises:

a. first and second comparators each having one input coupled to said first and second pulse storage registers respectively and the other input coupled to said counting means whereby if the output of said counting means representing the actual number of 60 Hz pulses occurring between heartbeats is greater than the number of pulses stored in said first register or less than the number of pulses stored in said second register, a warning signal is produced by the corresponding comparator.

7. A pulse monitor as in claim 6 wherein said means for storing a predetermined number of pulses in said first and second pulse storage registers comprises:

a. switch means coupled to said pulse divider means and said first and second pulse storage registers for selectively coupling said reduced pulses to a predetermined one of said storage registers, and b. means for coupling said selected reduced number of output pulses to said arithmetic means whereby said display indicates the heart rate represented by the count being stored in said selected first or second pulse storage register.

8. A pulse monitor as in claim 7 further including:

a. means for disconnecting the output of said clock circuit to said counting means whenever said switching means for selectively storing pulses in said first and second storage registers is actuated.

9. A pulse monitor as in claim 3 further comprising switch means for selectively coupling the output of said clock circuit and said arithmetic means to said display unit whereby either time of day or heartbeat rate may be selectively displayed.

10. A pulse monitor comprising:

a. a body portion adapted to be attached to and worn about the wrist with a strap, b. a sensor mounted in said body portion for detecting a heartbeat, c. a transducer coupled to said sensor for producing an electrical signal for each detected heartbeat, d. a source of electrical pulses of predetermined frequency, e. first and second storage means alternately coupled to said pulse source and said transducer for storing only said pulses occurring between electrical signals from said transducer representing successive heartbeats, f. arithmetic means alternately coupled to said first and second storage means for converting said stored pulses occurring only between each two successive heartbeats to a heatbeat rate, and g. display means coupled to said arithmetic means for visually displaying said rate.

11. A heart pulse monitor for the human body comprising:

a. a device for engagement with a part of said human body, b. a sensor in said device for detecting a heartbeat in a region of said part of said human body engaged by said device where a heartbeat is expected to normally occur, c. a transducer coupled to said sensor for converting each detected heartbeat to an electrical signal, d. a source of electrical pulses of predetermined frequency, e. means coupled to said transducer and said pulse source for receiving all of said pulses occurring between successive heartbeats and converting said pulses occurring only between each two successive heartbeats to a heartbeat rate, and f. display means coupled to said converting means for displaying said heartbeat rate.

12. A heartbeat pulse monitor for the human body comprising:

a. a pulse generator, b. a heartbeat detector, c. means coupled to said pulse generator and said detector for receiving all of said pulses occurring between successive heartbeats and converting only said pulses occurring between each two successive heartbeats to a heartbeat rate, and d. means coupled to said converting means for visually displaying said heartbeat rate.

13. A combination clock and heartbeat pulse monitor for the human body comprising:

a. a pulse generator, b. a heartbeat detector, c. means coupled to said pulse generator and said detector for receiving all of said pulses occurring between successive heartbeats and converting only said pulses occurring between each two successive heartbeats to a heartbeat rate as an output, d. a clock circuit coupled to said pulse generator for producing time-of-day signals as an output, e. a display, and f. means coupled to said converting means, said clock circuit and said display for selectively connecting either the heartbeat rate output of said converting means or said time-of-day output signals to said display for visual observation.

14. A heartbeat pulse monitor comprising:

a. a pulse generator, b. a heartbeat detector, c. means coupled to said pulse generator and said detector for receiving all of said pulses occurring between successive heartbeats and converting only said pulses occurring between each two successive heartbeats to an actual heartbeat rate, d. means coupled to said converting means for visually displaying said heartbeat rate,
e. means coupled to said pulse generator for storing pulses representing upper and lower desired heartbeat rate limits,
f. comparator means coupled to said converting means and said pulse storage means for comparing said converted pulses representing actual heartbeat rate to said stored pulses representing upper and lower desired heartbeat rate limits and producing a signal if either limit is reached, and
g. means coupled to said comparator for giving an alarm if said signal is produced.

* * * * *